United States Patent [19]

Fiege et al.

[11] 4,238,625
[45] Dec. 9, 1980

[54] PROCESS FOR THE PREPARATION OF ARYLOXYACETIC ACID

[75] Inventors: Helmut Fiege, Leverkusen; Karlfried Wedemeyer, Cologne, both of Fed. Rep. of Germany

[73] Assignee: Bayer Aktiengesellschaft, Leverkusen, Fed. Rep. of Germany

[21] Appl. No.: 92,783

[22] Filed: Nov. 8, 1979

[30] Foreign Application Priority Data

Nov. 30, 1978 [DE] Fed. Rep. of Germany ....... 2851788

[51] Int. Cl.³ ............................................. C07C 51/16
[52] U.S. Cl. .................................................... 562/421
[58] Field of Search ........................................ 562/421

[56] References Cited

U.S. PATENT DOCUMENTS 3,919,305  11/1975  Gay ..................................... 562/421

Primary Examiner—Alan Siegel
Attorney, Agent, or Firm—Sprung, Felfe, Horn, Lynch & Kramer

[57] ABSTRACT

In a process for the preparation of an aryloxyacetic acid by oxidation of aryloxyethanol of the formula

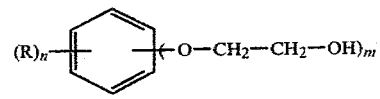

(I)

wherein
  m represents 1 or 2,
  n represents the numeral which results from the difference (6-m) and
  R either individually or independently of one another represent hydrogen, alkyl, cycloalkyl, aryl, aralkyl, alkoxy, cycloalkoxy, aryloxy, hydroxyl, halogen, alkylcarbonyl, arylcarbonyl, carboxyl or nitro, or represent a benzene ring or cycloalkane ring fused to the phenyl ring, with oxygen or an oxygen-containing gas in an aqueous alkaline medium at a temperature from 0° C. to the boiling point of the reaction mixture in the presence of platinum metals and/or palladium metals containing catalyst, the improvement which comprises carrying out the oxidation in the additional presence of an activator of lead and/or bismuth and/or a compound thereof and optionally in the additional presence of Cadmium and/or its compounds.

19 Claims, No Drawings

PROCESS FOR THE PREPARATION OF ARYLOXYACETIC ACID

The invention relates to a process for the preparation of aryloxyacetic acids by oxidation of aryloxyethanols.

It is known from Ullmann, Enzyklopädie der Technischen Chemie (Encyclopaedia of Industrial Chemistry), 4th edition, volume 9, 578 (1975), to prepare aryloxyacetic acids industrially by heating the corresponding aryloxy compounds (for example phenols or naphthols) with monochloroacetic acid in excess aqueous sodium hydroxide solution and then treating the mixture with hydrochloric acid. Disadvantages of the processes are, inter alia, that the chloroacetic acid must be employed in excess in order to compensate for losses, and that ultimately only sodium chloride is produced from all the chlorine required for the preparation of the chloroacetic acid.

The oxidation of aryloxyethanol with oxygen or air has also already been investigated repeatedly (Russian Patent 130,510, Zh. Prikl. Khim (Leningrad) 46, 2691 to 2694), Kinetika i Kataliz 1 (1960), 125 to 128 and Kinetika i Kataliz 2 (1961), 245). However, the results are unsatisfactory in respect of the reaction conditions, the yield and the catalyst productivity. Hitherto, the best results are achieved by oxidation with air in an aqueous alkaline medium over platinum/active charcoal catalysts containing from 2.5 to 10% of platinum (Zh. Fiz. Khim 42 (1968), 266 to 268). The best known yields of phenoxyacetic acid achieved according to this process are 82% of the theoretical conversion in the oxidation of phenoxyethanol and 88% of the theoretical conversion in the oxidation of 2,4-dichlorophenoxyethanol.

A precondition for these results are very low phenoxyethanol concentrations in the starting mixture (only 2.5% by weight), high pressures (140 bar), temperatures of 140° or 100° C. and a fresh catalyst. If the catalyst is re-used, the yield falls to 60% of the theoretical conversion. The phenoxyethanol which is not converted to the corresponding phenoxyacetic acid is lost by oxidative degradation to carbon dioxide and the starting phenol.

Apart from the industrially unfavorable conditions, such as low concentration of starting material, oxidation under high pressure and insufficient selectivity, a substantial disadvantage of the process resides in the low productivity (activity) of the platinum/active charcoal catalyst, which at 2.5% and 10% platinum content is respectively only 0.5 and 0.6 kg of phenoxyacetic acid per kg of catalyst and per hour (corresponding respectively to 20 and 6 kg of phenoxyacetic acid per kg of platinum and per hour). This means that in order to achieve short reaction times, very large amounts of the valuable platinum catalyst (relative to the phenoxyethanol) must be employed and correspondingly high losses in handling must be tolerated. Small amounts of catalyst result in very long reaction times.

A process has been found for the preparation of aryloxyacetic acids by oxidizing aryloxyethanols of the formula

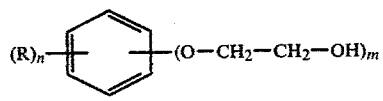

wherein
m represents 1 or 2,
n represents the numeral which results from the difference (6-m) and
R either individually or independently of one another represent hydrogen, alkyl, cycloalkyl, aryl, aralkyl, alkoxy, cycloalkoxy, aryloxy, hydroxyl, halogen, alkylcarbonyl, arylcarbonyl, carboxyl or nitro, or represent a benzene ring or cycloalkane ring fused to a phenyl ring, with oxygen or oxygen-containing gases in aqueous alkaline media at temperatures of from 0° C. to the boiling point of the reaction mixture in the presence of platinum metal catalysts, characterised in that the oxidation is carried out in the presence of lead and/or bismuth and/or their compounds and optionally in the additional presence of cadmium and/or its compounds.

The process according to the invention can be illustrated by the example of the following equation:

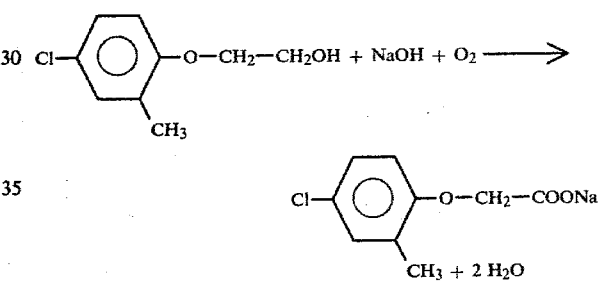

Alkyl radicals can be straight-chain or branched hydrocarbon radicals with 1 to 12, preferably 1 to 6, carbon atoms. Preferred alkyl radicals for the process according to the invention are lower alkyl radicals. Examples of alkyl radicals which may be mentioned are methyl, ethyl, propyl, isopropyl, butyl, isobutyl, sec.-butyl, tert.-butyl, pentyl, isopentyl, tert. amyl, hexyl, isohexyl, heptyl, isoheptyl, tert.-octyl, isooctyl, nonyl, isononyl, decyl, isodecyl, undecyl, isoundecyl, dodecyl and isododecyl.

Cycloalkyl radicals can be cyclic hydrocarbon radicals with 4 to 9, preferably 5 and 6, carbon atoms. The cyclopentyl and the cyclohexyl radical may be mentioned as examples.

The phenyl and the naphthyl radical may be mentioned as preferred aryl radicals for the process according to the invention.

Aralkyl radicals can be alkyl radicals with 1 to 6 carbon atoms, preferably lower alkyl radicals, which are substituted by an aromatic hydrocarbon radical with 6 to 12 carbon atoms, preferably phenyl and naphthyl. Benzyl, α-methyl-benzyl and α,α-dimethyl-benzyl groups may be mentioned by way of example.

Alkoxy radicals can consist of up to 12, preferably of up to 6, carbon atoms in the aliphatic part. A lower alkoxy radical is particularly preferred. The following may be mentioned as examples of alkoxy radicals: methoxy, ethoxy, propoxy, isopropoxy, butoxy, isobutoxy, tert.-butoxy, pentoxy, isopentoxy, hexoxy, isohexoxy and methylenedioxy.

The cyclopentoxy and the cyclohexoxy radical may be mentioned as preferred cycloalkoxy radicals.

The phenoxy and the naphthoxy radical may be mentioned as preferred aryloxy radicals.

Halogens can be fluorine, chlorine, bromine and iodine, preferably chlorine and bromine.

Lower alkylcarbonyl radicals ($C_1$ to $C_6$), such as the acetyl radical, may be mentioned as preferred alkylcarbonyl radicals.

The benzoyl radical may be mentioned as a preferred arylcarbonyl radical.

Fusion of a benzene ring to the phenyl ring can, for example, produce the naphthalene ring system.

Fusion of a cycloalkane ring to the phenyl ring can, for example, produce the tetralin ring system.

It is of course possible for the abovementioned substituents to be substituted by usual radicals which are inert under the reaction conditions. Fluorine, chlorine, methyl and methoxy may be mentioned as examples.

Aryloxyethanols, in which m is 1 and n is 1, 2 or 3 are particularly preferred for the process according to the invention.

Aryloxyethanols of the formula

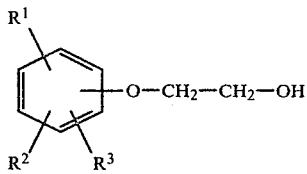

wherein
$R^1$, $R^2$ and $R^3$ are identical or different and represent hydrogen, lower alkyl, lower alkoxy, phenyl, naphthyl, phenoxy, lower alkylcarbonyl, fluorine and chlorine
are in particular preferred for the process according to the invention.

The preparation of the aryloxyethanols is in itself known.

For example, the aryloxyethanols can be prepared by addition reaction of ethylene oxide with the hydroxyl group or groups of an appropriately substituted phenol or naphthol (Monatshefte Chemie 77, (1947) 80 to 85).

The following aryloxyethanols may be mentioned specifically: phenoxyethanol, 2-methyl-phenoxyethanol, 3-methyl-phenoxyethanol, 4-methyl-phenoxyethanol, 2,3-dimethyl-phenoxyethanol, 2,4-dimethyl-phenoxyethanol, 2,5-dimethyl-phenoxyethanol, 2,6-dimethyl-phenoxyethanol, 3,4-dimethylphenoxyethanol, 3,5-dimethyl-phenoxyethanol, 2-chlorophenoxyethanol, 3-chloro-phenoxyethanol, 4-chloro-phenoxyethanol, 2-chloro-4-methyl-phenoxyethanol, 2-chloro-5-methyl-phenoxyethanol, 2-chloro-6-methyl-phenoxyethanol, 4-chloro-2-methyl-phenoxyethanol, 4-chloro-3-methyl-phenoxyethanol, 2-chloro-4-fluoro-phenoxyethanol, 2,3-dichlorophenoxyethanol, 2,4-dichlorophenoxyethanol, 2,5-dichloro-phenoxyethanol, 2,6-dichloro-phenoxyethanol, 3,4-dichloro-phenoxyethanol, 3,5-dichloro-phenoxyethanol, 4,6-dichloro-2-methyl-phenoxyethanol, 2,6-dichloro-4-methyl-phenoxyethanol, 2,6-dichloro-3-methyl-phenoxyethanol, 2,4-dimethyl-6-chloro-phenoxyethanol, 2,6-dimethyl-4-chloro-phenoxyethanol, 3,5-dimethyl-4-chloro-phenoxyethanol, 2,4,5-trichloro-phenoxyethanol, 2,4,6-trichloro-phenoxyethanol, 3,4,5-trichloro-phenoxyethanol, 2,3,4-trichloro-phenoxyethanol, 4-nonyl-phenoxyethanol, α-naphthoxyethanol and β-naphthoxyethanol. Preferred aryloxyethanols for the process according to the invention are phenoxyethanol, 4-chloro-2-methyl-phenoxyethanol, 2,4-dichloro-phenoxyethanol and 2,4,5-trichloro-phenoxyethanol.

According to the process of the invention, the oxidation of the aryloxyethanols to the aryloxyacetic acids is carried out in the presence of activators of lead and/or bismuth and/or their compounds, and optionally in the additional presence of cadmium and/or its compounds.

The advantages achieved by means of the invention are that as a result of the presence of the metals to be used according to the invention the selectivity, the activity and the re-usability of the catalyst are very substantially increased. Hence, very high yields can be achieved, the amount of catalyst, relative to aryloxyethanol, can be substantially reduced, the working pressure can be substantially reduced and the starting concentrations of the aryloxyethanols can also be appreciably increased. The platinum metal catalysts are completely inactive or inselective for the process according to the invention if used in the absence of the activators. They only become detectably active or selectrive after the addition, according to the invention, of lead of bismuth. As a result of the additional presence, according to the invention, of cadmium, both the activity and the selectivity of the catalyst are increased yet further.

The amounts in which the activators to be used according to the invention are employed can vary within wide limits. The activator effect manifests itself distinctly even on addition of as little as $5\times10^{-6}$ mol of metal or metal compound per mol of aryloxyethanol. One can also employ 0.1 mol or more of activator per mol of aryloxyethanol, but these high added amounts in general offer no advantage. In general, additions of $1\times10^{-5}$ to $10^{-1}$ mol, preferably $5\times10^{-5}$ to $5\times10^{-2}$ mol, of metal or metal compound per mol of aryloxyethanol to be oxidised have proved suitable.

The metals to be used as activators, particularly bismuth and/or lead, according to the invention can be employed in the elemental form and/or in the form of their compounds, for example as oxides, hydroxides, salts of hydracids, such as chlorides, bromides, iodides, sulphides, selenides and telurides, or as salts of inorganic oxy-acids, such as nitrates, nitrites, phosphites, sulfates, phosphates, carbonates, perchlorates, antimonates, arsenates, selenites, selenates and borates, or as salts of oxy-acids of the transition metals, such as vanades, niobates, tantalates, chromates, molybdates, tunstates and permanganates, or as salts of organic aliphatic or aromatic acids, such as, for example, formates, acetates, propionates, benzoates, salicylates, lactates, aryloxyacetates and citrates, when cadmium is additionally present it can be present in elemental form or in the form of a compound thereof, including any of the types of compounds named above.

The activators can in each case be soluble, partially soluble or insoluble in the reaction mixture.

Combinations of these activators with one another and/or with other elements of the compounds, not mentioned as activators, may also be employed.

The activators for the process according to the invention can be present in different valency levels and also mixed in valency levels. Furthermore, changes in the valency can occur during the reaction. If the activators are not added as oxides and/or hydroxides from the start, it is possible that they will become entirely or partially converted to these in an alkaline medium. After the reaction, the platinum metal catalyst together with the sparingly soluble activator can be filtered off and be re-used in further oxidation reactions. Losses of platinum metal catalysts and/or activators, if any, must be replaced.

The activator can be added as a solid, preferably in a finely divided form, or in the form of a solution, to the reactants. One can also add the activator already during the preparation of the platinum metal catalyst, or impregnate the platinum metal catalyst with the activator. The activator can also be employed as a carrier material for the platinum metal.

By platinum metals, and/or palladium metals which can be employed as catalysts for the process according to the invention, there are to be understood the chemically closely related metals platinum, palladium, rhodium, iridium, ruthenium and osmium, which in nature mostly occur together. Preferably platinum or palladium are employed as catalysts.

The platinum metals used as catalysts can be added to the reactants in a great variety of forms, for example in the form of the element, for instance as so-called black, in combination with other platinum metals or in the form of compounds, for example as oxides or in the form of other compounds.

The platinum metals can also be applied to a support. As examples of supports there may . . . active charcoal, graphite, kieselguhr, silica gel, spinels, aluminum oxide, asbestos, calcium carbonate, magnesium carbonate, barium sulphate or organic support materials.

Particularly preferred supports are pulverulent active charcoals, for example, pulverulent so-called medicinal charcoal, or pulverulent active charcoals produced from wood, such as are used for decolourising purposes.

The platinum metal content of the supported catalysts can vary within wide limits. Supported catalysts with a platinum metal content of less than 25% by weight have proved particularly suitable. Palladium-containing supported catalysts having a palladium content of 1 to 20% by weight, and platinum-containing supported catalysts having a platinum content of 0.1 to 5% by weight are particularly preferred.

The amounts in which the platinum metal catalysts are used, relative to the aryloxyethanol, can vary within wide limits. The amounts depend, inter alia, on the desired rate of oxidation. In general, their amount is less than the amount of aryloxyethanol in the starting mixture. In general, amounts of less than 30% by weight, in particular amounts of 0.5 to 20% by weight, relative to the aryloxyethanol, are employed.

The process according to the invention can usually be carried out by bringing oxygen or oxygen-containing gases, such as air, into good contact with the aqueous solution (or suspension) of the aryloxyethanol, which also contains the alkaline agent, the platinum metal catalyst and the activator (or, optionally, several activators). In general, the reaction is carried out at atmospheric pressure (1 bar), but oxidation can also be carried out at higher or lower pressures. In general, the process according to the invention is carried out in the pressure range of 0.5–10 bar.

The course of the reaction can be followed from the amount of oxygen taken up and is stopped when the amount of oxygen theoretically required for the desired aryloxyacetic acid has been taken up. In most cases, the uptake of oxygen ceases of its own accord, or slows down, in this stage. The progress of the reaction can also be followed in other ways, for example by determining the aryloxyethanol consumed or determining the aryloxyacetic acid formed.

For working up, the platinum metal catalyst and the undissolved activator are separated off, for example, by filtration. The resulting alkali metal salt solutions of the aryloxyacetic acid are then worked up in accordance with known methods (Ullman, Enzyklopädie der Technischen Chemie (Encyclopaedia of Industrial Chemistry), 4th edition, volume 9, pages 578 to 580).

The sequence in which the platinum metal catalyst, the activator, the aqueous alkali and the aryloxyethanol are brought together is optional. Thus, the platinum metal catalyst and the activator can be added to the mixture or solution of aqueous alkali and aryloxyethanol. One can also first take the platinum metal catalyst and the activator (or the activators) and add the mixture of aqueous alkali and aryloxyethanol. Finally, one can also first take the platinum metal catalyst, a part of the aqueous alkali and the activator (or the activators) and then add the aryloxyethanol together with the remaining alkali. Further, it is also possible to add the activator (or the activators) to the mixture of the reactant.

The concentration of the aryloxyethanol in the aqueous alkaline reaction mixture is in general selected so that the resulting aryloxyacetic acid is present in solution during the reaction. Concentrations of 2 to 25% by weight are advantageous. If desired, the solubility can be improved by the addition of inert solvents or solubilizing agents.

It is also possible to oxidize mixtures of different aryloxyethanols.

The oxidation according to the process of the invention is preferably carried out in the presence of alkalis, for example of sodium hydroxide or potassium hydroxide. The amount of alkali is in that case so chosen as to provide 0.5 to 10, preferably 0.8 to 8, especially 1 to 6, mols of alkali per mol of carboxyl group formed. The most advantageous amount of alkali in each individual case depends, inter alia, on the platinum metal, the aryloxyethanol, the activator or the activator combination and can easily be determined in preliminary experiments.

The possible reaction temperature for the process according to the invention can lie between the solidification point and the boiling point of the reaction mixture.

The reaction temperature to be used in each individual case depends inter alia on the catalyst system, the alkali concentration, the material properties of the educts and of the products, and the technical circumstances (desired rate of reaction, and removal of heat). The temperature range of about 20° to 100° C. is preferred for the process according to the invention.

Aryloxyacetic acids of the formula

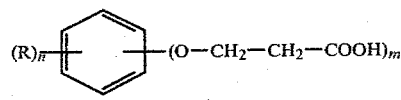

wherein
m and n have the abovementioned meaning can be prepared in accordance with the process of the invention.

Aryloxyacetic acids are valuable organic intermediate products and are of great importance as herbicides (Chemie der Pflanzenschutz- und Schädlingsbekämpfungsmittel (Chemistry of Plant Protection Agents and Pesticides), volume 2, pages 273 to 278 (1970); Römpps Chemie-Lexicon (Römpps Chemical Encyclopaedia), 7th edition, volume 4, page 2623 (1974)).

EXAMPLE 1

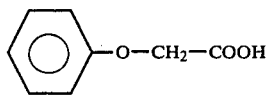

0.65 g of palladium-containing active charcoal (so-called medicinal charcoal containing 5% by weight of palladium), 0.025 g of solid $Bi(NO_3)_3.5H_2O$ (corresponding to an amount of bismuth of $5.2 \times 10^{-5}$ mol), 100 ml of 1.1 N sodium hydroxide solution and 13.8 g (0.1 mol) of phenoxyethanol are introduced into a reaction vessel which is provided with a stirrer, internal thermometer and gas inlet and can be thermostatically controlled by means of an outer jacket.

After displacing the air from the reaction vessel by means of oxygen, the stirrer is started, the reaction mixture is brought to 90° C. and pure oxygen is introduced, under normal pressure, into the mixture at this temperature. After 1.5 hours, when 0.1 mol of oxygen has been taken up, the oxidation stops.

After filtering the solution whilst still warm to remove the catalyst, and rinsing the latter with a small amount of water, the "neutral substances" (phenol and unconverted phenoxyethanol) were determined by bringing the filtrate to pH 6.5 with 20% strength sulphuric acid, extracting with ether and evaporating the combined ether extracts after drying over $Na_2SO_4$. The "residue from the pH 6.5 phase" was in this case negligibly small. To determine the phenoxyacetic acid, the aqueous phase (the filtrate) was subsequently acidified to pH 1 with 20% strength $H_2SO_4$, extracted as above, and the extract evaporated. The "residue from the pH 1 phase" consisted, in the present case, of 15.2 g of white crystalline phenoxyacetic acid which according to acidimetric determination was >99% pure and had a melting point of 98.5° to 99° C. The yield was thus virtually 100% of theory.

This type of working up has merely analytical greenness. One can also filter off the sodium salt of the phenoxyacetic acid, which is sparingly soluble in the cold, directly after cooling the filtrate, or liberate the phenoxyacetic acid, which is sparingly soluble in water, directly by acidification, and separate it off.

The catalyst, separated off as described above, is re-used in the next batch, and so on. Even on the 33rd re-use, the catalyst still gave the same yield of phenoxyacetic acid (100% of theory). The experiments were then discontinued.

EXAMPLE 2

The procedure followed is an in Example 1, except for the difference that instead of bismuth $5 \times 10^{-4}$ mol of lead in the form of an 0.1 M $Pb(NO_3)_2$ solution is added to the reaction mixture.

In this case, the oxygen uptake ceases after 1.75 hours, when about 0.1 mol of $O_2$ has been taken up. Working up gives about 1 g of "neutral substances" from the "pH 6.5 phase" and about 14.1 g of >99% pure phenoxyacetic acid, of melting point 98.5°-99° C., from the "pH 1 phase". The yield is accordingly 93% of theory.

EXAMPLE 3 (Comparative Example)

The procedure followed is as in Example 1, except for the difference that neither lead nor bismuth is added as an activator to the reaction mixture.

In this case, the uptake of about 0.1 mol of $O_2$ requires about 10 hours, and the oxygen uptake has not yet ceased after this time.

If, after the stoichiometric amount of $O_2$ has been taken up, the mixture is worked up, the working up of the "pH 6.5 phase" gives 6.7 g of "neutral substances", which according to gas chromatography consist predominantly of phenol, and the working up of the "pH 1 phase" gives only 6.3 g of an impure phenoxyacetic acid of melting point 93.5° to 96° C. (yield about 40% of theory).

Example 3 shows that without the addition of the activators according to the invention the reaction time over palladium is distinctly increased, the yield is greatly reduced as a result of oxidative degradation to phenol, and the quality of the phenoxyacetic acid obtained is less good.

EXAMPLES 4 to 11

The procedure of Example 1 is followed, except for the difference that the amount of activator, the sodium hydroxide solution concentration, the amount of phenoxyethanol and/or the temperature are varied. The volume of sodium hydroxide solution employed, the amount of catalyst and the type of activator remain the same. The conditions and results are summarised in Table 1.

TABLE 1

Oxidation of phenoxyethanol over 0.65 g of palladium-containing active charcoal (5% of palladium on medicinal charcoal) in the presence of bismuth as the activator, in 100 ml of sodium hydroxide solution, by means of oxygen under normal pressure, until 1 mol of $O_2$ has been taken up per mol of phenoxyethanol

| Example No. | Phenoxyethanol Amount g | Normality of the NaOH mol/l | Amount of activator $(Bi(NO_3)_3)$ mol | Temp. °C. | Time for $O_2$ uptake hours | Phenoxyacetic acid | | |
|---|---|---|---|---|---|---|---|---|
| | | | | | | pH 1 phase amount g | Melting point °C. | Yield % of theory |
| 4 | 13.8 | 4 | $1 \times 10^{-5}$ | 70 | 11 | 13.6 | 98.5–99 | 90 |
| 5 | 13.8 | 4 | $1 \times 10^{-4}$ | 70 | 4 | 15 | 98.5–99 | 99 |
| 6 | 13.8 | 4 | $1 \times 10^{-3}$ | 70 | 4.5 | 14.9 | 98.5–99 | 98 |
| 7 | 13.8 | 2 | $5 \times 10^{-5}$ | 90 | 2 | 15.2 | 98.5–99 | 100 |
| 8 | 13.8 | 4 | $5 \times 10^{-5}$ | 95 | 3.3 | 15.2 | 98.5–99 | 100 |
| 9 | 17.25 | 1.4 | $5 \times 10^{-5}$ | 90 | 2.3 | 19 | 98.5–99 | 100 |
| 10 | 20.7 | 1.7 | $5 \times 10^{-5}$ | 90 | 9.8 | 22.8 | 98.5–99 | 100 |

TABLE 1-continued

Oxidation of phenoxyethanol over 0.65 g of palladium-containing active charcoal (5% of palladium on medicinal charcoal) in the presence of bismuth as the activator, in 100 ml of sodium hydroxide solution, by means of oxygen under normal pressure, until 1 mol of $O_2$ has been taken up per mol of phenoxyethanol

| Example No. | Phenoxy- ethanol Amount g | Normality of the NaOH mol/l | Amount of activator (Bi(NO$_3$)$_3$) mol | Temp. °C. | Time for $O_2$ uptake hours | Phenoxyacetic acid pH 1 phase amount g | Melting point °C. | Yield % of theory |
|---|---|---|---|---|---|---|---|---|
| 11 | 27.6 | 2.2 | $5 \times 10^{-5}$ | 90 | 22.7 | 30 | 98.5–99 | 99 |

EXAMPLES 12 to 17

The apparatus and procedure correspond to Example 1. 0.65 g of platinum-containing active charcoal (so-called decolourising charcoal, containing 1% by weight of platinum), 100 ml of 5 N sodium hydroxide solution, 13.8 g (0.1 mol) of phenoxyethanol, 0.0005 mol of lead (II) nitrate (as an 0.5 M solution) or 0.0005 mol of bismuth (III) nitrate (as Bi(NO$_3$)$_3$.5H$_2$O) as the activator and, optionally, 0.0001 mol of cadmium (II) nitrate (in the form of an 0.1 M solution) as an additional activator (Examples 14 and 15) are introduced into the oxidation vessel.

Comparative Example 16 is carried out completely without activators whilst in Comparative Example 17 only cadmium is added.

After displacing the air from the oxidation-according the mixture is warmed to 70° C. and at this temperature oxygen is stirred into the reaction mixture under normal pressure. The results are summarised in Table 2.

TABLE 2

Influence of addition of lead, bismuth and cadmium on the oxidation of 0.1 mol of phenoxyethanol over platinum-containing active charcoal (for conditions, see text) in 100 ml of 5 N sodium hydroxide solution

| Example No. | Acti- vator | Ad- ditional activator | $O_2$ uptake amount mol | $O_2$ uptake time hours | Products Phenol$^{(a)}$ amount g | Phenoxyacetic acid Amount$^{(b)}$ g | Phenoxyacetic acid Yield % of theory |
|---|---|---|---|---|---|---|---|
| 12 | Pb | none | 0.1 | 6 | 5.6 | 5.2 | 34 |
| 13 | Bi | none | 0.1 | 6 | 5.3 | 5.3 | 35 |
| 14 | Pb | Cd | 0.1 | 3.5 | 0.3 | 14.9 | 98 |
| 15 | Bi | Cd | 0.11 | 6 | 4.1 | 8.1 | 53 |
| 16 | none | none | 0.00 | 6 | Phenoxyethanol recovered | | 0 |
| 17 | none | Cd | 0.00 | 6 | virtually unchanged | | 0 |

$^{(a)}$Extract residue from "pH 6.5 phase": main component phenol, accompanied by unconverted phenoxyethanol
$^{(b)}$Extract residue from "pH 1 phase"

As is shown by Comparative Example 16 in Table 2, phenoxyethanol is virtually not oxidised, under the selected conditions, over the catalyst which only contains 1% of platinum. Oxidation only occurs if lead or bismuth are present in the reaction mixture (Examples 12 and 13). A further improvement in the oxidation results is achieved if additionally cadmium is present in the reaction mixture (Examples 14 and 15). Cadmium alone does not act as an activator for the platinum-containing active charcoal (Comparative Example 17).

EXAMPLES 18 to 19

If the procedure of Example 14 is followed, but at 50° or 60° C. instead of 70° C., the reaction times are respectively 5 and 3 hours and the yields of phenoxyacetic acid are in both cases 100% of theory (melting point 98.5° to 99° C.).

EXAMPLE 20

If the procedure of Example 19 is followed, at 60° C., but with the difference that the $5 \times 10^{-4}$ mol of lead are not introduced into the reaction mixture in the form of a lead (II) nitrate solution, but in the form of a fine powder of
(a) lead metal
(b) lead (II) oxide
(c) lead (II) sulphate
(d) lead (II) acetate or
(e) lead (II,IV) oxide (red lead),
the reaction time is in all cases again about 3 hours and the phenoxyacetic acid yield virtually 100% of theory.

EXAMPLES 21 to 31

The procedure of Example 1 is followed. In each case, 0.05 mol of aryloxyethanol is oxidised in 100 ml of 5% strength by weight sodium hydroxide solution at 90° C. by means of pure oxygen under normal pressure over 0.65 g of palladium-containing active charcoal (medicinal charcoal) containing 10% by weight of palladium, in the presence of $5 \times 10^{-5}$ mol of bismuth (III) nitrate.

Table 3 summarises the results achieved with various aryloxyethanols. Since the same reaction conditions were used in every case, the results do not necessarily represent the optimum.

TABLE 3

Oxidation of various aryloxyethanols (for conditions, see text)

| Example No. | Aryloxyethanol Name | Amount used g | Time required for uptake of 0.05 mol of $O_2$ | Aryloxyacetic acid Name | Yield $g^{(a)}$ | Yield % of theory |
|---|---|---|---|---|---|---|
| 21 | 4-Methyl-phenoxyethanol | 7.6 | $0.75^{(c)}$ | 4-Methyl-phenoxyacetic acid | 8.2 | 99 |
| 22 | 3,4-Dimethyl-phenoxyethanol | 8.3 | 1.0 | 3,4-Dimethyl-phenoxyacetic acid | 8.6 | 95 |
| 23 | 4-tert.-Butyl-phenoxyethanol | 9.7 | 0.75 | 4-tert.-Butyl-phenoxyacetic acid | 10.3 | 98 |
| 24 | 4-Chloro-phenoxyethanol | 8.6 | 1.25 | 4-Chlorophenoxyacetic acid | 8.7 | 94 |
| 25 | 4-Chloro-2-methyl-phenoxyethanol | 9.3 | 2.0 | 4-Chloro-2-methyl-phenoxyacetic acid | 9.8 | 98 |
| 26 | 4-Chloro-3,5-dimethyl-phenoxyethanol | 10.0 | 1.0 | 4-Chloro-3,5-dimethyl-phenoxyacetic acid | 9.9 | 92 |
| 27 | 2,4-Dichloro-phenoxyethanol | 10.3 | 1.75 | 2,4-Dichloro-phenoxyacetic acid | 10.5 | 95 |
| 28 | 2,4,5-Trichloro-phenoxyethanol | 12.1 | 1.5 | 2,4,5-Trichloro-phenoxyacetic acid | 12.3 | 96 |
| 29 | 4-Nitro-phenoxyethanol | 9.1 | 4.5 | 5-Nitro-phenoxyacetic acid | $3.8^{(b)}$ | 33 |
| 30 | 4-Methoxy-phenoxyethanol | 8.4 | 1.0 | 4-Methoxy-phenoxyacetic acid | 8.8 | 97 |
| 31 | β-Naphthoxyethanol | 9.4 | 2.5 | β-Naphthoxyacetic acid | | |

$^{(a)}$Only "pH 1 phase"; according to titrimetric determination virtually always 99 to 100% pure.
$^{(b)}$Only about 85% pure.
$^{(c)}$Over 0.65 g of active charcoal containing 5% of palladium the reaction time is doubled but the yield is the same (99% of theory).

What is claimed is:

1. In a process for the preparation of an aryloxyacetic acid by oxidation of an aryloxyethanol of the formula

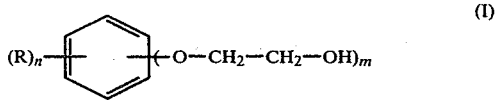

(I)

wherein
m represents 1 or 2,
n represents the numeral which results from the difference (6-m) and
R either individually or independently of one another represent hydrogen, alkyl, cycloalkyl, aryl, aralkyl, alkoxy, cycloalkoxy, aryloxy, hydroxyl, halogen, alkylcarbonyl, arylcarbonyl, carboxyl or nitro, or represent a benzene ring or cycloalkane ring fused to the phenyl ring,
with oxygen or an oxygen-containing gas in an aqueous alkaline medium at a temperature from 0° C. to the boiling point of the reaction mixture in the presence of platinum metals and/or palladium metals containing catalyst, the improvement which comprises carrying out the oxidation in the additional presence of an activator of lead and/or bismuth and/or a compound thereof and optionally in the additional presence of cadmium and/or its compounds.

2. A process according to claim 1 wherein the lead and/or bismuth and optionally additional cadmium is present in amounts of between $1 \times 10^{-5}$ and $1 \times 10^{-1}$ mol of metal or metal compound per mol of aryloxyethanol to be oxidized are employed.

3. A process according to claim 1 wherein lead and/or bismuth and optionally additional Cadmium is present in amounts of $5 \times 10^{-5}$ to $5 \times 10^{-2}$ mol of metal or metal compound per mol of aryloxy-ethanol to be oxidized.

4. A process according to claim 1 wherein the oxidation is carried out in the presence of a platinum-containing catalyst.

5. A process according to claim 1 wherein the oxidation is carried out in the presence of a palladium containing catalyst.

6. A process according to claim 4 and to claim 5 wherein the process is carried out in the presence of a lead or lead containing compound.

7. A process according to claim 4 and to claim 5 wherein the process is carried out in the presence of bismuth or a bismuth containing compound.

8. A process according to claim 1 wherein the process is carried out in the presence of a platinum and/or Palladium catalysts supported catalyst.

9. A process according to claim 1 wherein the process is carried out in the presence of a platinum and/or Palladium catalysts disposed on an active charcoal support.

10. A process according to claim 10 and claim 11 wherein the platinum- or Palladium-content of the supported catalyst is less than 25 percent by weight.

11. A process according to claim 1 wherein the process is carried out in the presence of a platinum and/or palladium supported catalyst wherein the catalyst contains less than 25 percent by weight palladium and/or less than 5 percent by weight platinum.

12. A process according to claim 1 wherein the process is carried out in the presence of elemental lead.

13. A process according to claim 1 wherein the process is carried out in the presence of elemental bismuth.

14. A process according to claim 1 wherein the process is carried out in the presence of a lead compound.

15. A process according to claim 1 wherein the process is carried out in the presence of a bismuth compound.

16. A process according to claim 14 wherein said lead compound is a lead oxide, hydroxide, salt of hydracid, salt of inorganic oxy-acid, salt of oxy-acid of a transition metal, salt of organic aliphatic or aromatic acid, or phenolate.

17. A process according to claim 15 wherein said bismuth compound is a bismuth oxide, hydroxide, salt of hydracid, salt of inorganic oxy-acid, salt of oxy-acid of a transition metal, salt of organic aliphatic or aromatic acid, or phenolate.

18. A process according to claim 14 wherein said lead compound is a lead oxide, hydroxide, chloride, bromide, iodide, sulfide, selenide, telluride, nitrate, nitrite, phosphite, sulfate, phosphate, carbonate, perchlorate, antimonate, arsenate, selenite, selenate, borate, vanadate, niobate, tantalate, chromate, molybdate, tungstate, permanganate, formate, acetate, propionate, benzoate, salicylate, lactate, aryloxyacetate, citrate, or phenolate.

19. A process according to claim 15 wherein said bismuth compound is a bismuth oxide, hydroxide, chloride, bromide, iodide, sulfide, selenide, telluride, nitrate, nitrite, phosphite, sulfate, phosphate, carbonate, perchlorate, antimonate, arsenate, selenite, selenate, borate, vanadate, niobate, tantalate, chromate, molybdate, tungstate, permanganate, formate, acetate, propionate, benzoate, salicylate, lactate, aryloxyacetate, citrate, or phenolate.

* * * * *